(12) United States Patent
Kim et al.

(10) Patent No.: US 12,383,742 B2
(45) Date of Patent: Aug. 12, 2025

(54) HEADACHE AND PAIN RELIEF DEVICE DUE TO TEMPOROMANDIBULAR JOINT DISEASE

(71) Applicant: PTBRO Inc., Busan-si (KR)

(72) Inventors: Tae Hun Kim, Busan (KR); Won Sik Bae, Busan (KR); Jae Hyeong Oh, Busan (KR); Dong Jin You, Busan (KR)

(73) Assignee: PTBRO Inc., Busan-si (KR)

( * ) Notice: Subject to any disclaimer, the term of this patent is extended or adjusted under 35 U.S.C. 154(b) by 0 days.

(21) Appl. No.: 18/533,192

(22) Filed: Dec. 8, 2023

(65) Prior Publication Data
US 2024/0100340 A1    Mar. 28, 2024

Related U.S. Application Data

(63) Continuation of application No. 18/240,570, filed on Aug. 31, 2023, which is a continuation of application No. PCT/KR2023/002365, filed on Feb. 18, 2023.

(30) Foreign Application Priority Data

Feb. 23, 2022   (KR) ......................... 10-2022-0023359

(51) Int. Cl.
*A61H 23/02*    (2006.01)
*A61N 1/04*     (2006.01)
*A61N 1/36*     (2006.01)

(52) U.S. Cl.
CPC ......... *A61N 1/36075* (2013.01); *A61H 23/02* (2013.01); *A61N 1/0472* (2013.01);
(Continued)

(58) Field of Classification Search
CPC ............ A61N 1/36021; A61N 1/36075; A61N 1/36071; A61N 1/0484; A61N 1/0456;
(Continued)

(56) References Cited

U.S. PATENT DOCUMENTS 1,487,998 A * 3/1924 Woolf .................. A61N 1/0472
                                                    607/139
1,849,745 A * 3/1932 Hoffman .................. A61N 1/06
                                                    607/139
(Continued)

FOREIGN PATENT DOCUMENTS

KR         10-1530772 B1     6/2015
KR      10-2018-0064781 A    6/2018
(Continued)

OTHER PUBLICATIONS

English translation of Jin (KR 100821299 B1) (Year: 2008).*
English translation of KR 20130013064 A (Year: 2013).*

*Primary Examiner* — Justine R Yu
*Assistant Examiner* — Christopher E Miller
(74) *Attorney, Agent, or Firm* — NKL Law; Jae Youn Kim

(57) ABSTRACT

A device for relieving headache and pain caused by temporomandibular joint disorders, the device including a body having a neck band worn on a user's neck, first connectors extending forwardly from both ends of the neck band by first set lengths, and second connectors extending upwardly from front ends of the first connectors by second set lengths; first low frequency electrostimulators disposed on the second connectors and coming into close contact with the temporalis muscles, when the body is worn on the user's head, to apply low frequencies to the temporalis muscles; and second low frequency electrostimulators disposed on the connected portions between the first connectors and the second connectors and coming into close contact with the masseter muscles, when the body is worn on the user's head, to apply low frequencies to the masseter muscles.

9 Claims, 6 Drawing Sheets

(52) U.S. Cl.
CPC ....... *A61N 1/0484* (2013.01); *A61N 1/36196* (2013.01); *A61H 2201/1604* (2013.01)

(58) Field of Classification Search
CPC .... A61N 2005/0645; A61N 2005/0647; A61H 2201/1604; A61H 2201/1607; A61H 2201/165; A61H 2205/02; A61H 2205/021; A61H 2205/028; A61H 39/04
See application file for complete search history.

(56) References Cited

U.S. PATENT DOCUMENTS

| | | | | |
|---|---|---|---|---|
| 3,620,219 | A * | 11/1971 | Barker | A61N 1/321 |
| | | | | 607/139 |
| 3,659,614 | A * | 5/1972 | Jankelson | A61N 1/321 |
| | | | | 607/139 |
| 3,709,228 | A * | 1/1973 | Barker | A61N 1/0472 |
| | | | | 607/139 |
| 3,851,651 | A * | 12/1974 | Icenbice, Jr. | A61N 1/36034 |
| | | | | 377/122 |
| 4,233,986 | A * | 11/1980 | Tannenbaum | A61N 1/36021 |
| | | | | 607/66 |
| 5,421,799 | A * | 6/1995 | Rabin | A61H 7/006 |
| | | | | 601/79 |
| 5,611,771 | A * | 3/1997 | Taylor | A61H 23/0263 |
| | | | | 601/48 |
| 6,077,237 | A * | 6/2000 | Campbell | G06F 3/011 |
| | | | | 607/139 |
| 6,179,794 | B1 * | 1/2001 | Burras | A61H 23/0263 |
| | | | | 601/79 |
| 6,638,295 | B1 * | 10/2003 | Schroer | A61H 39/04 |
| | | | | 606/204.15 |
| 8,142,373 | B1 * | 3/2012 | Riles | A61H 23/02 |
| | | | | 601/48 |
| 9,532,915 | B1 * | 1/2017 | McKinney | A61H 1/00 |
| 2003/0045922 | A1 * | 3/2003 | Northrop | A61N 1/328 |
| | | | | 607/139 |
| 2005/0267388 | A1 * | 12/2005 | Hanna | A61H 23/02 |
| | | | | 601/79 |
| 2010/0042138 | A1 * | 2/2010 | Duelo Riu | A61H 39/04 |
| | | | | 606/204 |
| 2011/0270141 | A1 * | 11/2011 | Ye | A61M 21/00 |
| | | | | 601/46 |
| 2012/0302929 | A1 * | 11/2012 | Tkachenko | A61H 23/0254 |
| | | | | 601/48 |
| 2013/0204169 | A1 * | 8/2013 | Poepperling | A61H 23/02 |
| | | | | 601/46 |
| 2015/0073316 | A1 * | 3/2015 | Bende | A61H 23/02 |
| | | | | 601/46 |
| 2015/0224019 | A1 * | 8/2015 | Barbera | A61H 23/02 |
| | | | | 601/46 |
| 2017/0165485 | A1 * | 6/2017 | Sullivan | A61B 5/0022 |
| 2017/0281940 | A1 * | 10/2017 | de Oliveira | A61N 1/36021 |
| 2017/0291007 | A1 * | 10/2017 | Dubey | A61H 23/0263 |
| 2019/0134390 | A1 * | 5/2019 | Shimada | A61N 1/36021 |
| 2019/0143114 | A1 * | 5/2019 | Nelson | A61H 39/00 |
| | | | | 607/3 |
| 2019/0232047 | A1 * | 8/2019 | Chu | A61H 23/00 |
| 2021/0315768 | A1 * | 10/2021 | Morra | A61H 15/0078 |
| 2024/0042203 | A1 * | 2/2024 | Gill | A61N 1/36025 |

FOREIGN PATENT DOCUMENTS

| | | |
|---|---|---|
| KR | 10-1920493 B1 | 11/2018 |
| KR | 10-2019-0128833 A | 11/2019 |
| KR | 10-2021-0075492 A | 6/2021 |
| KR | 10-2021-0117377 A | 9/2021 |

* cited by examiner

HEADACHE AND PAIN RELIEF DEVICE DUE TO TEMPOROMANDIBULAR JOINT DISEASE

TECHNICAL FIELD

The present invention relates to a device for relieving headache and pain caused by temporomandibular joint disorders, more specifically to a device for relieving headache and pain caused by temporomandibular joint disorders that is capable of relieving the tension type headache and pain caused by the temporomandibular joint disorders (TMJD).

BACKGROUND ART

The temporomandibular joints are the joints that connect the mandible (lower jaw) and the temporal bones (the skull) and are located in front of the ears. The temporomandibular joints act as center axes of all jaw movements and are supported by jaw muscles and ligaments. The disc of the temporomandibular joint functions as a cushion between the lower jaw and the skull. The temporomandibular joints, the muscles, the ligaments, the discs, and the lower jaw operate together to perform complex activities such as opening (mouth opening), chewing, speaking, swallowing, and the like, but the occurrence of abnormality in the functions of the temporomandibular joints due to various causes is called temporomandibular joint disorders.

A representative symptom of the temporomandibular joint disorders is pain in the lower jaw and in the muscles in front of the ears when a patient chews something or yawns. Whenever the patient opens the mouth, further, clicking sounds (joint noise) come from the temporomandibular joints, and the mouth and jaw move in the limited range.

The temporomandibular joint disorders are classified into disc displacement, arthritis, dislocation, and spasticity. The disc displacement is a state where the disc of the temporomandibular joint escapes from its original position. At an initial stage of the disc displacement, only a clicking sound comes from the temporomandibular joint when the patient opens and closes the mouth, without any additional symptoms, but as the disc displacement progresses, he or she feels jaw locked. If the disc displacement seriously progresses, he or she cannot open the mouth suddenly and feels serious pain in the temporomandibular joints. If arthritis occurs, the temporomandibular joints hurt, chewing or jaw movements are uncomfortable, and sometimes, crinkle sounds come from the temporomandibular joints. If arthritis seriously progresses, spasticity of the temporomandibular joints occurs to make the mouth not open well and hard to take foods. Since the temporomandibular joints and the jaw muscles have close functional relation with each other, arthritis and jaw muscle diseases may occur together, thereby causing muscle tension, myofascial pain, myositis, muscle cramps, muscle contracture, and the like. Among them, the muscle tension and the myofascial pain occur well when the fatigue of the muscle is accumulated, the myositis occurs by injury or inflammation, the muscle cramps occur well due to central causes or electrolyte disorder, and the muscle contracture is much influenced by various endocrine functions or psychological causes.

If muscle abnormalities are accompanied, it is hard to open the mouth or chew foods due to pain, and the pain may cause headache and spread to the neck, the shoulders, and the like.

Methods for treating the temporomandibular joint disorders include pharmacotherapy using painkiller, muscle relaxants, and the like, physical therapy using packing, transcutaneous electrical nerve stimulation, ultraviolet ray, high frequency electrode, low-level laser, and the like, and a surgical therapy. In specific, the high frequency electrode therapy and the low-level laser therapy, which are chiefly used in the physical therapy, relieve pain and show high treatment results, but require a therapy time of 30 minutes to one hour. In the case of the high frequency electrode therapy, further, the diseased part of the patient has to be continuously rubbed by a physical therapist, which causes inconveniences of use. In the case of the conventional therapies using light such as ultraviolet ray and low-level laser, the treatment is not transmitted to the deep portion of the temporomandibular joint, thereby failing to achieve proper treatment results.

Recently, a silver spike point electrode has been introduced as a headache and pain relief device for relieving tension type headache and pain caused by the temporomandibular joint disorders. This is an effective and safe pain relief device that causes silver spike point stimulation effectiveness using microcurrent.

However, the conventional device is bulky in size and has contact parts made of sharp metal, and to allow the contact parts to come into close contact with the diseased part of the patient, a compressor such as special cups for cupping therapy making use of negative pressure or hydrogel patches are used. Accordingly, it is hard that the conventional device comes into close contact with the hair or skin of the human body where a lot of sweat and moisture are generated.

Prior Art Literature

[Patent literature] Korean Patent Application Laid-open No. 10-2021-0075492

DISCLOSURE

Technical Problem

Accordingly, the present invention has been made in view of the above-mentioned problems occurring in the related art, and it is an object of the present invention to provide a device for relieving headache and pain caused by temporomandibular joint disorders that is capable of relieving the tension type headache and pain caused by the temporomandibular joint disorders.

It is another object of the present invention to provide a device for relieving headache and pain caused by temporomandibular joint disorders that is capable of being more compact in size than existing pain relief devices and thus conveniently used by white-collar workers and students.

The technical problems to be achieved through the present invention are not limited as mentioned above, and other technical problems not mentioned herein will be obviously understood by one of ordinary skill in the art through the following description. Objects and advantages of the present invention will be more clearly understood from the detailed description as will be described below and the attached drawings.

Technical Solution

To accomplish the above-mentioned objects, according to the present invention, a device for relieving headache and pain caused by temporomandibular joint disorders may include: a body (100) having a neck band (110) surroundingly worn on a user's neck, first connectors (120) extending forwardly from both ends of the neck band (110) by first set lengths, and second connectors (130) extending upwardly from front ends of the first connectors (120) by second set lengths; first low frequency electrostimulators (200) disposed on the second connectors (130) and coming into close contact with the temporalis muscles, when the body (100) is worn on the user's head, to apply low frequencies to the temporalis muscles; and second low frequency electrostimulators (300) disposed on the connected portions between the first connectors (120) and the second connectors (130) and coming into close contact with the masseter muscles, when the body (100) is worn on the user's head, to apply low frequencies to the masseter muscles.

According to the present invention, each first low frequency electrostimulator (200) may include: a first micro vibrator (210) for applying micro vibrations to the temporalis muscle when the body (100) is worn; and first conductive silicone rubber members (220) roundedly protruding from the first micro vibrator (210) toward the temporalis muscle to apply the low frequency to the temporalis muscle when the body (100) is worn.

According to the present invention, the first low frequency electrostimulators (200) may be disposed on the inner sides of the upper peripheries of the second connectors (130).

According to the present invention, the device may further include inclined portions (150) inclined inwardly from the upper peripheries of the second connectors (130), the first low frequency electrostimulators (200) being disposed on the inner sides of the inclined portions (150).

According to the present invention, the first conductive silicone rubber members (220) may be arranged to inverse triangular shapes on the inner sides of the inclined portions (150).

According to the present invention, each second low frequency electrostimulator (300) may include: a second micro vibrator (310) for applying micro vibrations to the masseter muscle when the body (100) is worn; and second conductive silicone rubber members (320) roundedly protruding from the second micro vibrator (310) toward the masseter muscle to apply the low frequency to the masseter muscle when the body (100) is worn.

According to the present invention, the second low frequency electrostimulators (300) may be disposed on the inner sides of the connected portions where the front ends of the first connectors (120) and the bottom ends of the second connectors (130) are crossingly connected to each other.

According to the present invention, the device may further include protruding portions (140) protruding inwardly by given lengths from the connected portions where the front ends of the first connectors (120) and the bottom ends of the second connectors (130) are crossingly connected to each other, the second low frequency electrostimulators (300) being disposed on the inner sides of the protruding portions (140).

According to the present invention, the second conductive silicone rubber members (320) may be arranged to square or rectangular shapes on the inner sides of the protruding portions (140).

According to the present invention, the device may further include a battery (600) built in the body (100) and connected to an external power supply (700) through a cable (610) in such a way as to be rechargeable if necessary.

According to the present invention, the device may further include: first expansion and contraction parts (400) disposed on the first connectors (120) in such a way as to expand and contract the lengths of the first connectors (120) in first set directions (W1) when the body (100) is worn; and second expansion and contraction parts (500) disposed on the second connectors (130) in such a way as to expand and contract the lengths of the second connectors (130) in second set directions (W2) when the body (100) is worn.

According to the present invention, the device may further include a controller for controlling the operations of the first low frequency electrostimulators (200) and the second low frequency electrostimulators (300) using at least one of the user's smartwatch (30) and smartphone (40).

Advantageous Effects

According to the present invention, the device can relieve the tension type headache and pain caused by the temporomandibular joint disorders.

Further, the device according to the present invention can be more compact in size than the existing pain relief devices and thus conveniently used by white-collar workers and students.

Furthermore, the device according to the present invention can operate the controller through applications of Internet of Things (IoT) using the user's smartwatch and smartphone by means of Bluetooth control, so that the device can be simpler in configuration and more lightweight when compared with the existing devices, and the intuitive control of the device can be performed even by general persons.

Furthermore, the device according to the present invention can improve the conductivity of the microcurrent to the contacted portions of the user therewith through the physical elasticity generated through the structural shape of the body and the soft contacts and appropriate pressure application of the conductive silicone rubber members, and the device according to the present invention can come into close contact with the hair or skin of the human body where a lot of sweat and moisture are generated.

The effectiveness of the invention is not limited as mentioned above, and it should be understood to those skilled in the art that the effectiveness of the invention may include another effectiveness as not mentioned above from the detailed description of the present invention.

MODE FOR INVENTION

Figure 1:
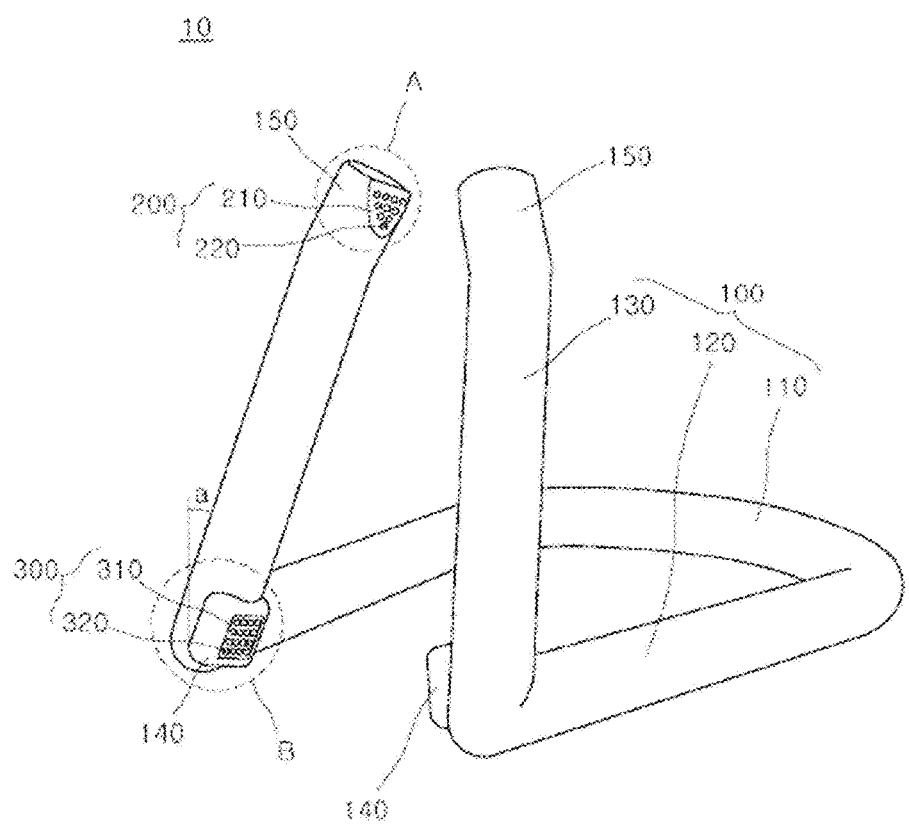
FIG. 1 is a schematic perspective view showing a device for relieving headache and pain caused by temporomandibular joint disorders according to the present invention.

Hereinafter, an embodiment of the present invention, which may be carried out easily by those having ordinary skill in the art, will be described with reference to the accompanying drawings. The embodiment of the present invention may be embodied in different forms and should not be construed as limited to the embodiments set forth herein.

In order to facilitate the general understanding of the present invention in describing the present invention, through the accompanying drawings, the same reference numerals will be used to describe the same components and an overlapped description of the same components will be omitted. The corresponding parts in the embodiments of the present invention are indicated by corresponding reference numerals even if they are shown in different drawings. If it is determined that the detailed explanation on the well known technology related to the present invention makes the scope of the present invention not clear, the explanation will be avoided for the brevity of the description.

Also, in explaining elements, terms like "first", "second", "A", "B", "(a)", "(b)", etc. may be used. However, such terms are used to distinguish one from the others only and they do not affect the essence, nature, sequence, order, etc. The term 'coupled' or 'connected', as used herein, is defined as connected, although not necessarily directly, and not necessarily mechanically. To the contrarily, the term 'directly coupled' or 'directly connected', as used herein, is defined as connected without having any component disposed therebetween.

For the convenience of the description, further, components may be dividedly explained, but they may be located in a single device or module. Otherwise, one component may be disposed on a plurality of devices or modules.

Hereinafter, an explanation of a device for relieving headache and pain caused by temporomandibular joint disorders according to the present invention will be given in detail with reference to the attached drawings.

Figure 2:
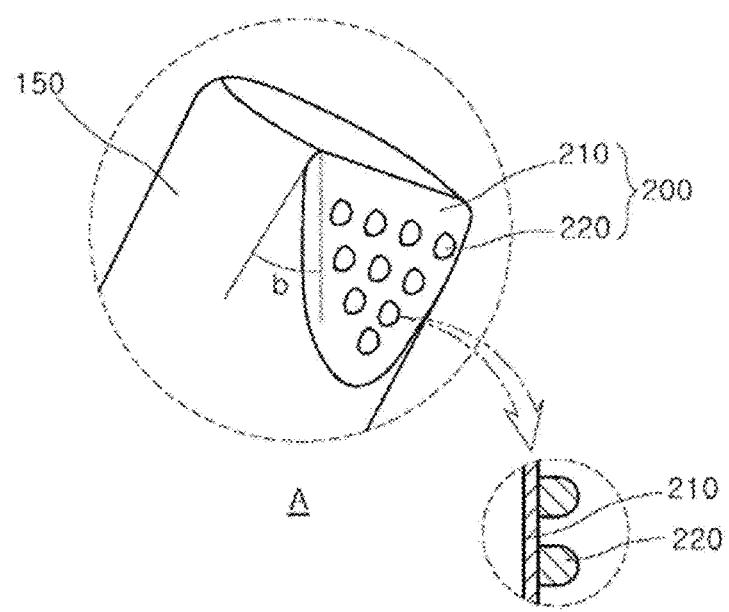
FIG. 2 is an enlarged perspective view showing a portion "A" of FIG. 1.
Figure 3:
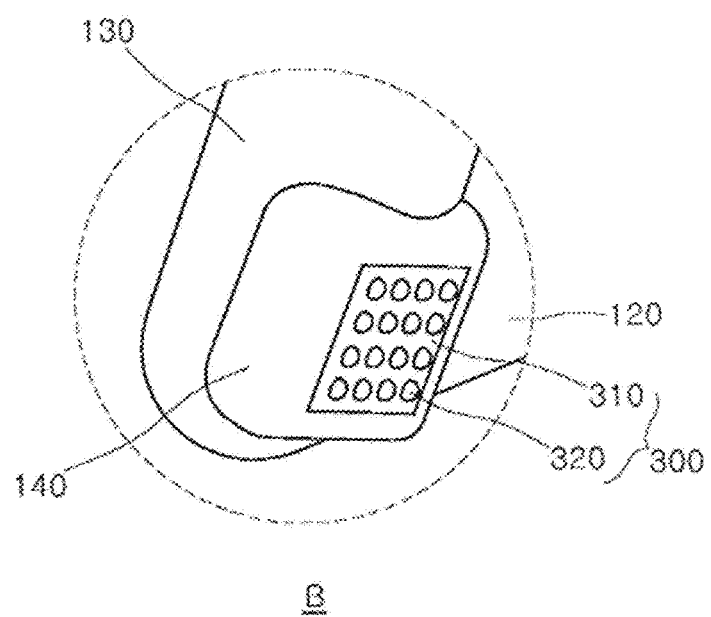
FIG. 3 is an enlarged perspective view showing a portion "B" of FIG. 1.
Figure 4:
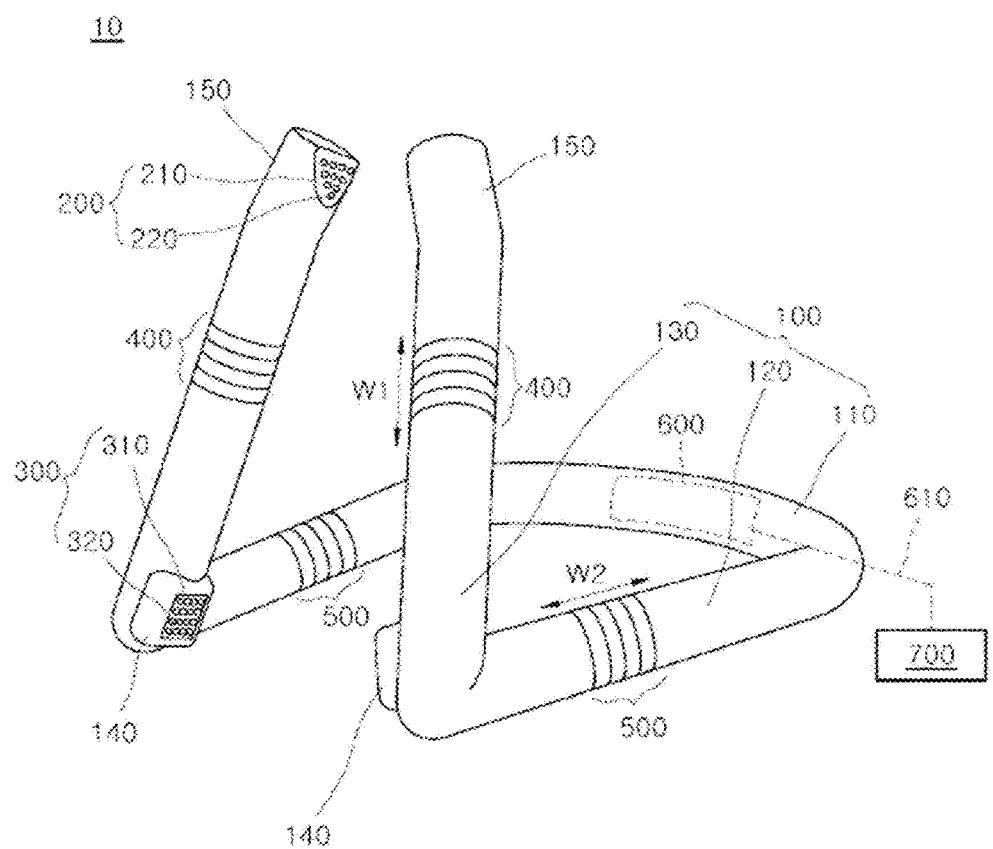
FIG. 4 is a perspective view showing the device for relieving headache and pain caused by temporomandibular joint disorders according to the present invention, wherein additional components are provided.
Figure 5:
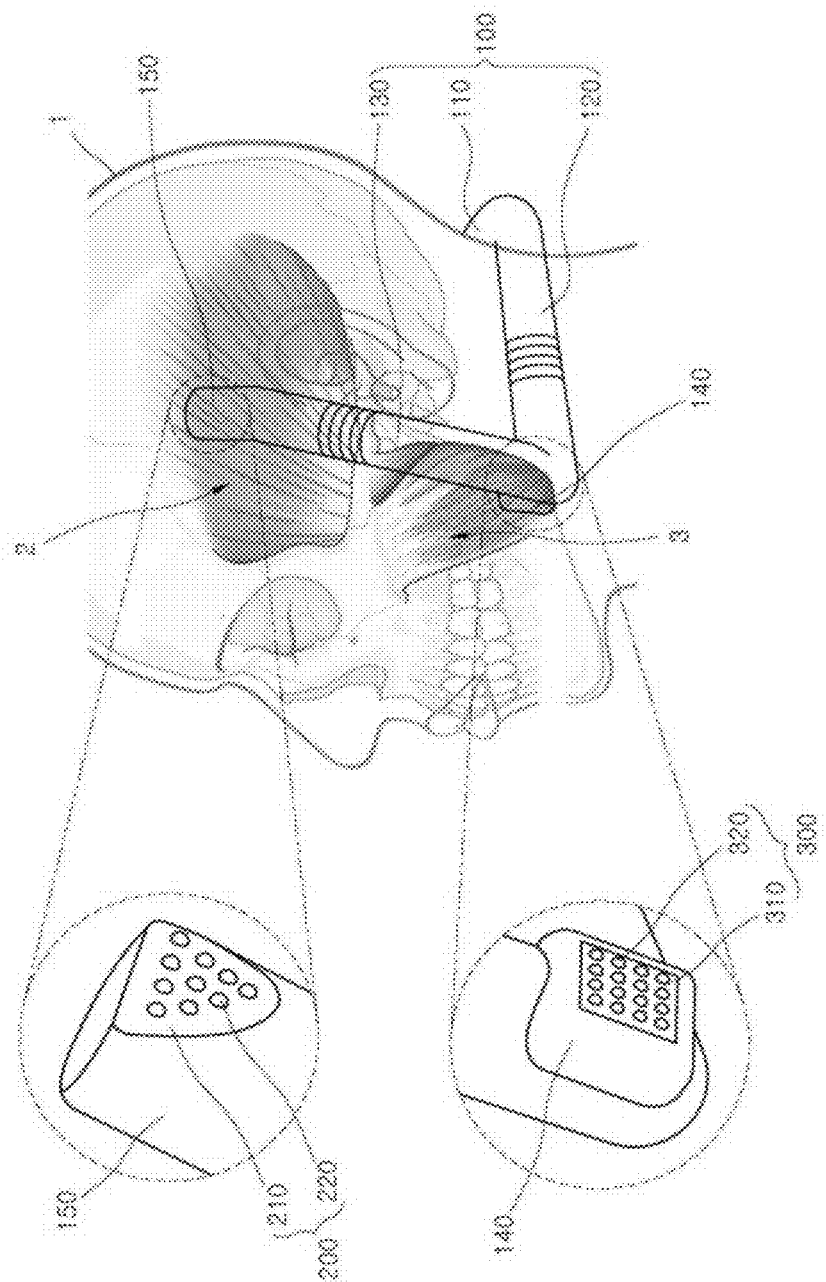
FIG. 5 is a perspective view showing a state where the device for relieving headache and pain caused by temporomandibular joint disorders according to the present invention is mounted on a user's head.
Figure 6:
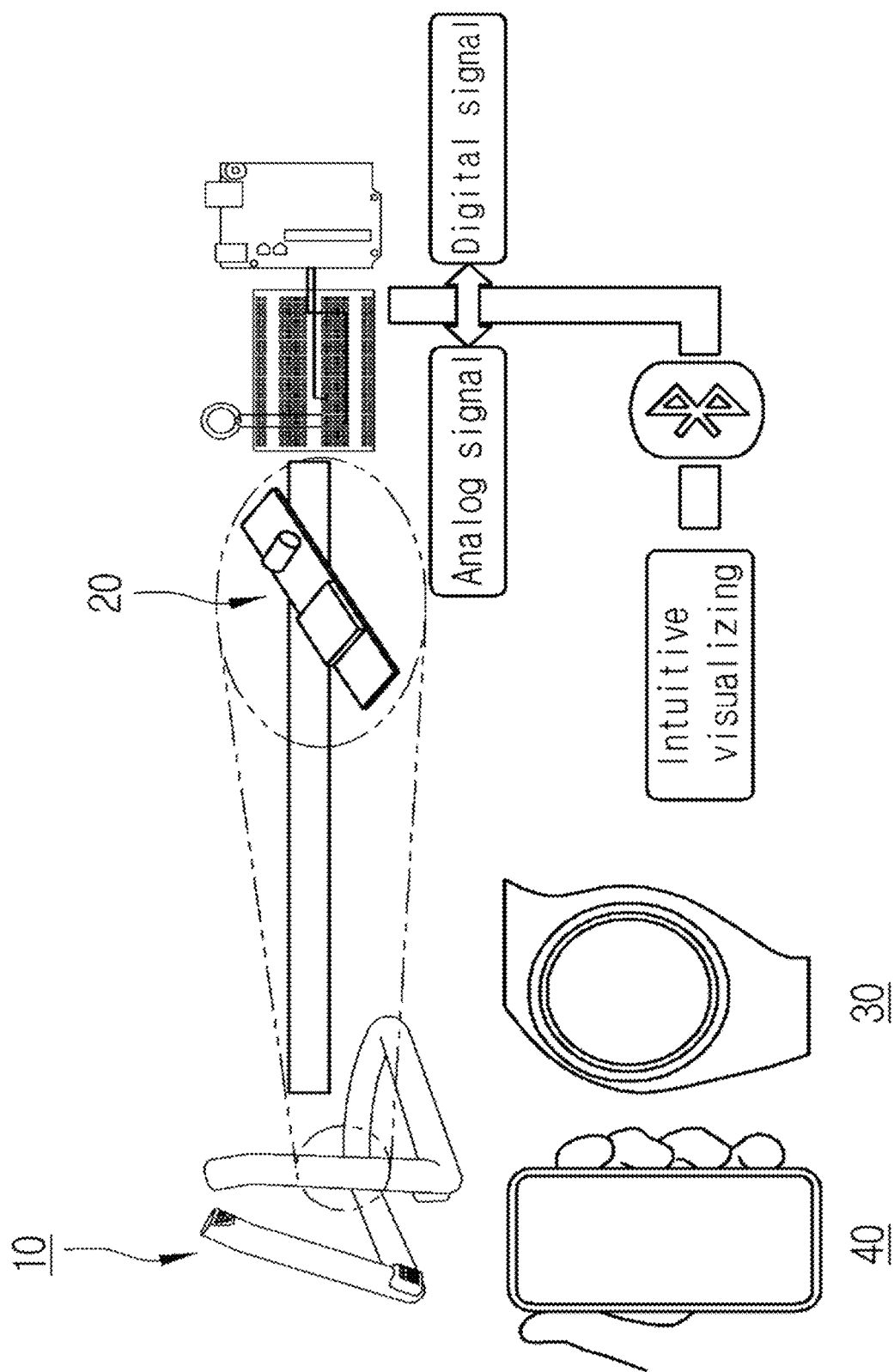
FIG. 6 is a block diagram showing a method for using the device for relieving headache and pain caused by temporomandibular joint disorders according to the present invention.

FIG. 1 is a schematic perspective view showing a device for relieving headache and pain caused by temporomandibular joint disorders according to the present invention, FIG. 2 is an enlarged perspective view showing a portion "A" of FIG. 1, FIG. 3 is an enlarged perspective view showing a portion "B" of FIG. 1, FIG. 4 is a perspective view showing the device for relieving headache and pain caused by temporomandibular joint disorders according to the present invention, wherein additional components are applied, FIG. 5 is a perspective view showing a state where the device for relieving headache and pain caused by temporomandibular joint disorders according to the present invention is mounted on a user's head, and FIG. 6 is a block diagram showing a method for using the device for relieving headache and pain caused by temporomandibular joint disorders according to the present invention.

As shown, a device 10 for relieving headache and pain caused by temporomandibular joint disorders according to the present invention includes a body 100, first low frequency electrostimulators 200, and second low frequency electrostimulators 300.

The body 100 includes a neck band 110, first connectors 120, and second connectors 130.

The neck band 110 is surroundingly worn on a user's neck and has the shape of C so that the back of the user's neck is surrounded therewith.

The first connectors 120 extend forwardly from both ends of the neck band 110 by first set lengths.

The second connectors 130 extend upwardly from front ends of the first connectors 120 by second set lengths. For example, the second connectors 130 are connected inclinedly to the first connectors 120 by an angle of 'a' with respect to vertical and upward directions from the first connectors 120.

The first low frequency electrostimulators 200 are disposed on the second connectors 130 and come into close contact with the temporalis muscles 2 (See FIG. 5), when the body 100 is worn on the user's head 1 (See FIG. 5), to apply low frequencies to the temporalis muscles 2.

The second low frequency electrostimulators 300 are disposed on the connected portions between the first connectors 120 and the second connectors 130 and come into close contact with the masseter muscles 3 (See FIG. 5), when the body 100 is worn on the user's head 1 (See FIG. 5), to apply low frequencies to the masseter muscles 3.

Each first low frequency electrostimulator 200 of the device 10 for relieving headache and pain according to the present invention includes a first micro vibrator 210 and first conductive silicone rubber members 220 (See FIG. 2).

The first micro vibrator 210 serves to apply micro vibrations to the temporalis muscle 2 when the body 100 is worn. To do this, a micro vibration motor is further provided.

The first conductive silicone rubber members 220 roundedly protrude from the first micro vibrator 210 toward the temporalis muscle 2 and apply the low frequency to the temporalis muscle 2 when the body 100 is worn. Referring to FIG. 2, the protruding shapes of the first conductive silicone rubber members 220 are hemispherical.

In specific, the first low frequency electrostimulators 200 are disposed on the inner sides of the upper peripheries of the second connectors 130.

Further, the device 10 for relieving headache and pain caused by temporomandibular joint disorders according to the present invention includes inclined portions 150 inclined inwardly from the upper peripheries of the second connectors 130.

The first low frequency electrostimulators 200 are disposed on the inner sides of the inclined portions 150. In specific, the first low frequency electrostimulators 200 are disposed on the inner sides of the inclined portions 150 in such a way as to be tapered by an angle of 'b'. Like this, since the second connectors 130 have such structural shapes applying physical elasticity, the first low frequency electrostimulators 200 are brought into contact with the skin, while having appropriate pressure.

For example, the first conductive silicone rubber members 220 are arranged to inverse triangular shapes on the inner sides of the inclined portions 150.

Each second low frequency electrostimulator 300 of the device 10 for relieving headache and pain according to the present invention includes a second micro vibrator 310 and second conductive silicone rubber members 320 (See FIG. 3).

The second micro vibrator 310 serves to apply micro vibrations to the masseter muscle 3 when the body 100 is worn. To do this, a micro vibration motor is further provided.

The second conductive silicone rubber members 320 roundedly protrude from the second micro vibrator 310 toward the masseter muscle 3 and apply the low frequency to the masseter muscle 3 when the body 100 is worn.

In specific, the second low frequency electrostimulators 300 are disposed on the inner sides of the connected portions where the front ends of the first connectors 120 and the bottom ends of the second connectors 130 are crossingly connected to each other.

Further, the device 10 for relieving headache and pain caused by temporomandibular joint disorders according to the present invention includes protruding portions 140 protruding inwardly by given lengths from the connected portions where the front ends of the first connectors 120 and the bottom ends of the second connectors 130 are crossingly connected to each other.

The second low frequency electrostimulators 300 are disposed on the inner sides of the protruding portions 140.

For example, the second conductive silicone rubber members 320 are arranged to square or rectangular shapes on the inner sides of the protruding portions 140.

Further, the device 10 for relieving headache and pain caused by temporomandibular joint disorders according to the present invention includes a rechargeable battery 600 (See FIG. 4).

For example, the battery 600 is built in the body 100 and connected to an external power supply 700 through a cable 610 if necessary, so that it is rechargeable. According to the present invention, advantageously, a sufficient space for the battery 600 is provided within the body 100, and the battery 600 is conveniently rechargeable at houses or offices using commonly known charging (e.g., C type charging).

Further, the device 10 for relieving headache and pain caused by temporomandibular joint disorders according to the present invention includes first and second expansion and contraction parts 400 and 500 adapted to change the size of the body 100 (See FIG. 4).

The first expansion and contraction parts 400 are disposed on the first connectors 120 to expand and contract the lengths of the first connectors 120 in first set directions W1 when the body 100 is worn.

The second expansion and contraction parts 500 are disposed on the second connectors 130 to expand and contract the lengths of the second connectors 130 in second set directions W2 when the body 100 is worn. Like this, as the first and second expansion and contraction parts 400 and 500 perform the length adjustment, advantageously, the size and shape of the body 100 are adjustable according to different head sizes of users.

Further, the device 10 for relieving headache and pain caused by temporomandibular joint disorders according to the present invention includes a controller for controlling the operations of the first low frequency electrostimulators 200 and the second low frequency electrostimulators 300 using at least one of the user's smartwatch 30 and smartphone 40. For example, convenient controlling through a portable application may be adopted (See FIG. 6).

The device 10 for relieving headache and pain caused by temporomandibular joint disorders according to the present invention operates by means of an inverter 20, and the controller controls a pre-stored application through Internet of Things (IoT) using the user's smartwatch 30 and smartphone 40 by means of Bluetooth control, so that the device 10 can be simpler in configuration and more lightweight when compared with the existing device.

As described above, the device 10 for relieving headache and pain caused by temporomandibular joint disorders according to the present invention can relieve the tension type headache and pain caused by the temporomandibular joint disorders. In specific, the device 10 according to the present invention is more compact in size than the existing pain relief device and thus conveniently used by white-collar workers and students.

Further, the device 10 according to the present invention can improve the conductivity of the microcurrent to the contacted portions of the user therewith through the physical elasticity generated through the structural shape of the body and the soft contacts and appropriate pressure application of the conductive silicone rubber members, and the device 10 according to the present invention can come into close contact with the hair or skin of the human body where a lot of sweat and moisture are generated.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

EXPLANATIONS OF REFERENCE NUMERALS

10: Device for relieving headache and pain caused by temporomandibular joint disorders
20: Inverter
30: Smartwatch
40: Smartphone
100: Body
110: Neck band
120: First connector
130: Second connector
140: Protruding portion
150: Inclined portion
200: First low frequency electrostimulator
210: First micro vibrator
220: First conductive silicone rubber member
300: Second low frequency electrostimulator
310: Second micro vibrator
320: Second conductive silicone rubber member
400: First expansion and contraction part
500: Second expansion and contraction part
600: Battery
610: Cable
700: External power supply

The invention claimed is:

1. A device for relieving headache and pain caused by temporomandibular joint disorders, the device comprising:
   a body having a neck band configured to partially surround a neck of a user, first connectors extending straight horizontally and forwardly from both ends of the neck band by first lengths, respectively, and second connectors extending straight upwardly from front ends of the first connectors by second lengths, respectively;
   first frequency electrostimulators respectively disposed on the second connectors and configured to come into contact with temporalis muscles, when the body is worn on a head of the user, to apply frequencies to the temporalis muscles; and
   second frequency electrostimulators respectively disposed on connected portions between the first connectors and the second connectors and configured to come into contact with masseter muscles, when the body is worn on the head of the user, to apply frequencies to the masseter muscles,
   wherein front ends of the first connectors and bottom ends of the second connectors are connected seamlessly, and both ends of the neck band and rear ends of the first connectors are connected seamlessly,
   wherein each first frequency electrostimulator comprises a first micro vibrator for applying micro vibrations to each of the temporalis muscles when the body is worn, wherein each second frequency electrostimulator comprises a second micro vibrator for applying micro vibrations to each of the masseter muscles when the body is worn, and wherein each first frequency electrostimulator is separate from each second frequency electrostimulator to apply the frequencies to the temporalis muscles and the masseter muscles, the device, further comprising:

first expansion and contraction parts disposed on the first connectors so as to expand and contract the first lengths of the first connectors respectively in directions of the first lengths;

second expansion and contraction parts disposed on the second connectors so as to expand and contract the second lengths of the second connectors respectively in directions of the second lengths; and protruding portions respectively disposed and protruding inwardly by given lengths from the connected portions where the front ends of the first connectors and the bottom ends of the second connectors are respectively connected to each other, the second frequency electrostimulators being disposed on inner sides of the protruding portions, wherein the first connectors are configured to be respectively disposed below ears of the user when the body is worn by the user.

2. The device according to claim 1, wherein each first frequency electrostimulator further comprises:

first conductive silicone rubbers configured to roundedly protrude from the first micro vibrator toward each of the temporalis muscles to apply the frequencies to each of the temporalis muscles when the body is worn.

3. The device according to claim 2, wherein the first frequency electrostimulators are disposed on inner sides of upper peripheries of the second connectors.

4. The device according to claim 2, further comprising inclined portions inclined inwardly from upper peripheries of the second connectors, the first frequency electrostimulators being disposed on inner sides of the inclined portions.

5. The device according to claim 4, wherein the first conductive silicone rubbers are arranged to inverse triangular shapes on the inner sides of the inclined portions.

6. The device according to claim 1, wherein each second frequency electrostimulator further comprises:

conductive silicone rubbers roundedly protruding from the second micro vibrator toward each of the masseter muscles to apply the frequencies to each of the masseter muscles when the body is worn.

7. The device according to claim 1, wherein each second frequency electrostimulator further comprises second conductive silicone rubbers, and wherein the second conductive silicone rubbers are arranged in square or rectangular shapes on the inner sides of the protruding portions.

8. The device according to claim 1, further comprising a rechargeable battery built in the body and connected to an external power supply through a cable.

9. The device according to claim 1, further comprising a controller for controlling operations of the first frequency electrostimulators and the second frequency electrostimulators using at least one of a smartwatch and a smartphone.

* * * * *